United States Patent [19]

Langham

[11] Patent Number: 4,883,056
[45] Date of Patent: Nov. 28, 1989

[54] PNEUMATIC PRESSURE PROBE

[75] Inventor: Maurice E. Langham, Timonium, Md.

[73] Assignee: Ocular Blood Flow Laboratories, Inc., Timonium, Md.

[21] Appl. No.: 117,235

[22] Filed: Nov. 5, 1987

[51] Int. Cl.⁴ .............................................. A61B 3/16
[52] U.S. Cl. .................................... 128/645; 128/748; 73/79
[58] Field of Search .............................. 128/645-652, 128/678, 748; 73/78-79, 756

[56] References Cited

U.S. PATENT DOCUMENTS

| | | | |
|---|---|---|---|
| 1,900,285 | 3/1933 | Huber | 128/678 |
| 3,272,001 | 9/1966 | Adise | 128/645 |
| 3,349,623 | 10/1967 | Pasten | 128/678 X |
| 3,703,095 | 11/1972 | Holcomb et al. | 128/645 |
| 3,714,819 | 2/1973 | Webb | 128/645 |
| 4,386,611 | 6/1983 | Kantorski et al. | 128/645 |

Primary Examiner—Angela D. Sykes
Attorney, Agent, or Firm—Dressler, Goldsmith, Shore, Sutker & Milnamow, Ltd.

[57] ABSTRACT

A pneumatic pressure probe is disclosed which provides rapid and accurate measurement of fluid pressure in an organ across a membrane but without pressurizing the organ itself. The pneumatic pressure probe includes a sensor head movably mounted by means of a hollow shaft to a handle that defines a pressure chamber. The sensor head defines a venting chamber within which is situated a thrust nozzle that communicates with the pressure chamber through the hollow shaft. Gas discharging from the thrust nozzle pressurizes the venting chamber and applies minimal force to an area of the epithelium across which the fluid pressure is determined. The pressure in the venting chamber is transmitted to the pressure chamber through the thrust nozzle and is monitored by means of a pressure transducer.

15 Claims, 5 Drawing Sheets

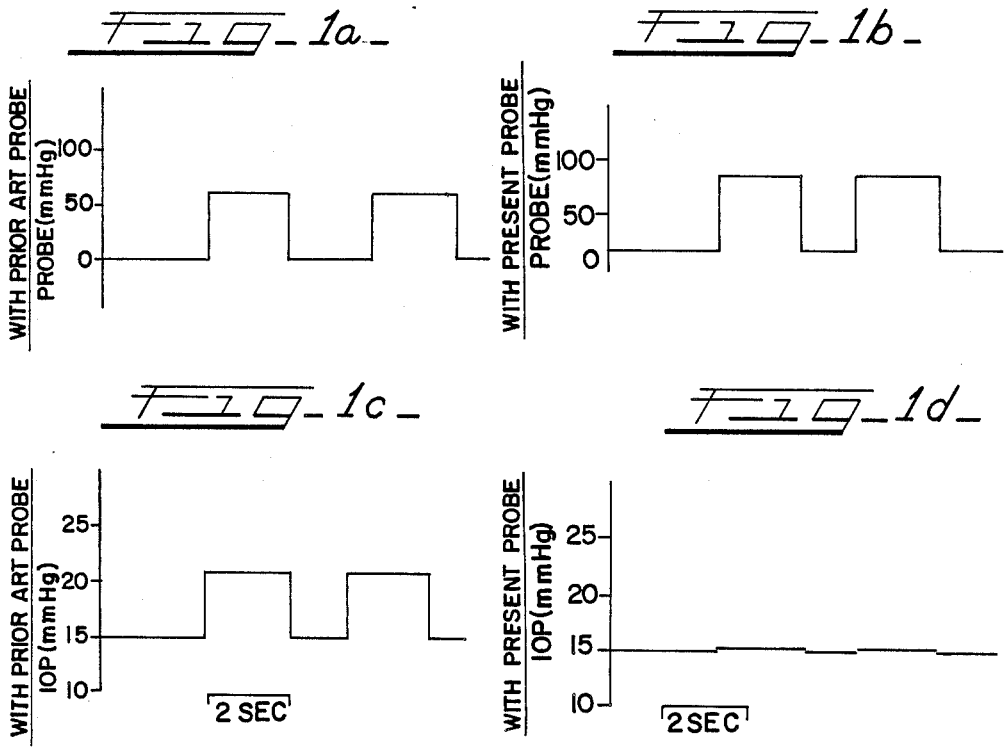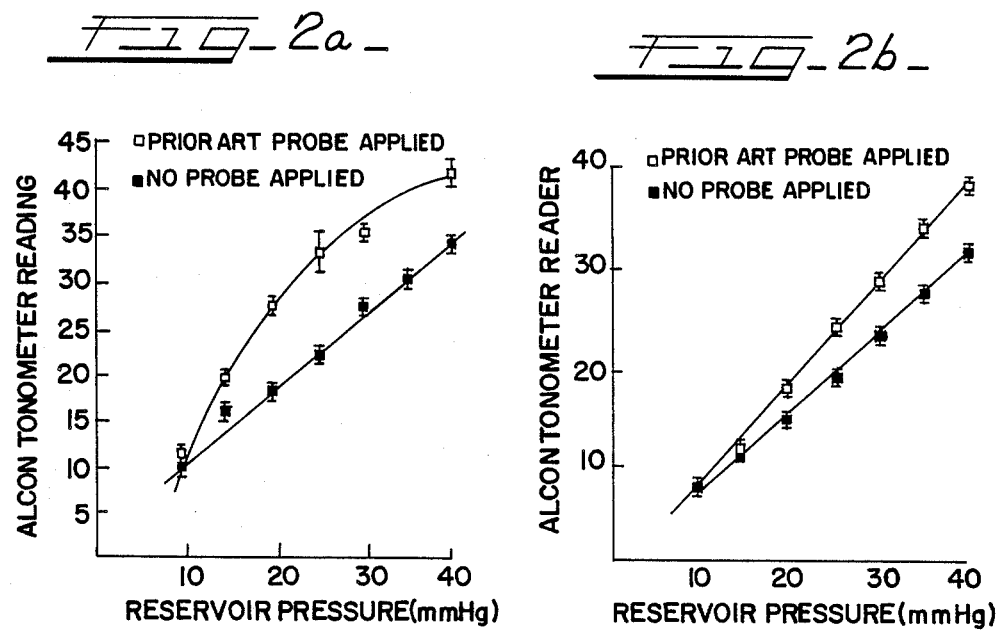

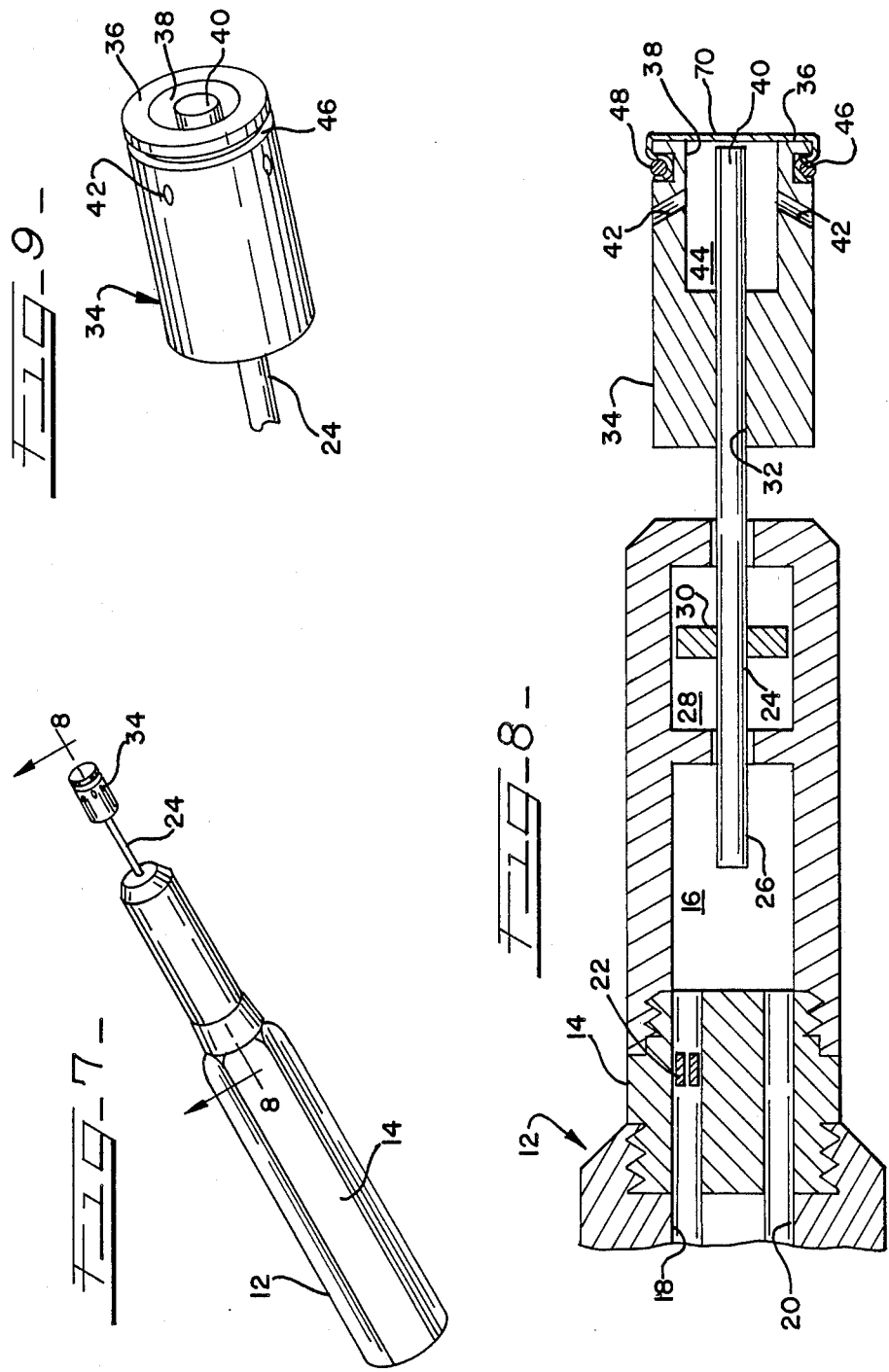

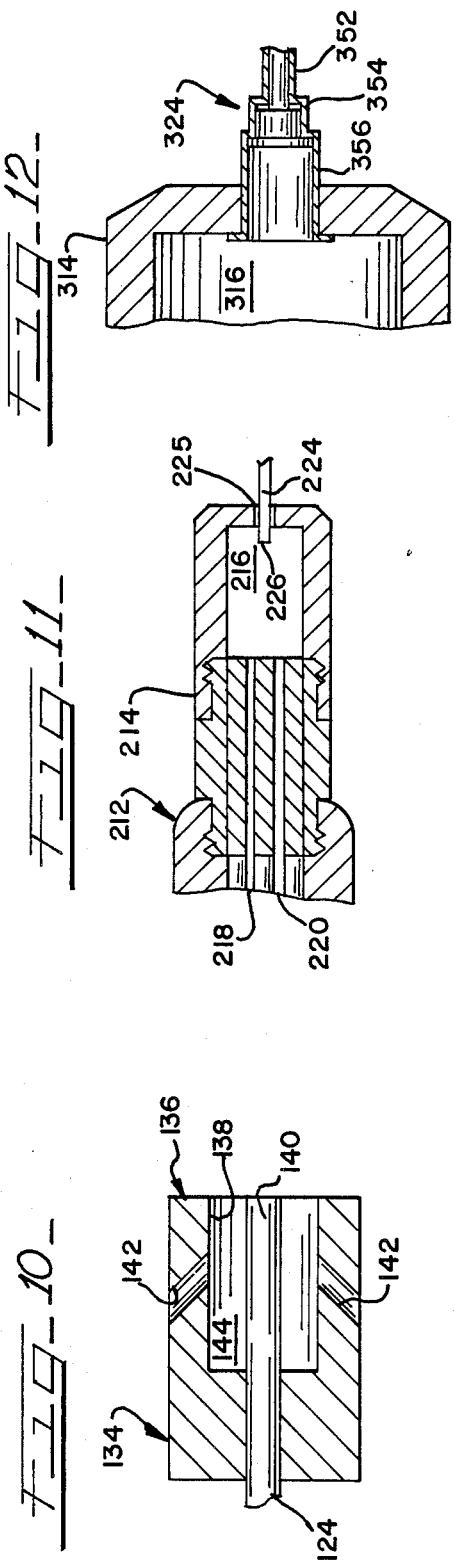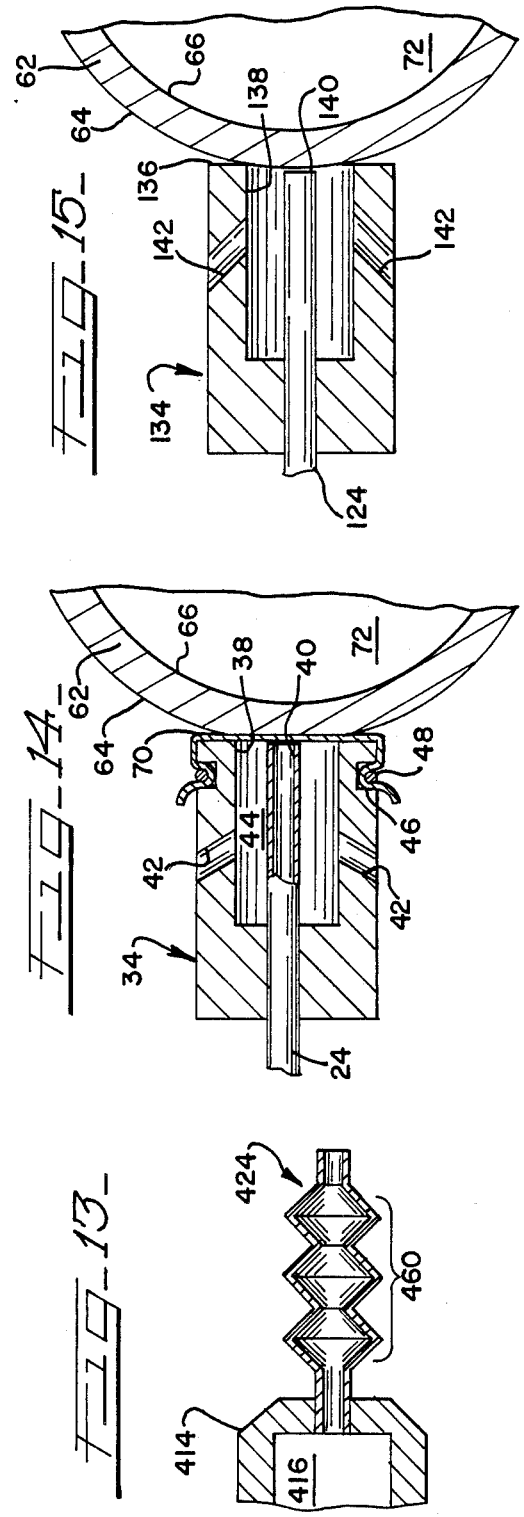

PNEUMATIC PRESSURE PROBE

DESCRIPTION

1. Technical Field

This invention relates to devices for use in measuring physiological fluid pressure and in particular to pneumatic pressure probes.

2. Background Art

Prior art pneumatic pressure probes, also known as tonometers, usually are applanation or force balance pressure sensing devices. Applanation type pressure sensors operate by measuring the force required to flatten a predetermined area on the surface encasing the fluid.

A representative prior art tonometer is shown in U.S. Pat. No. 3,714,819 to Webb. This device uses a pneumatically driven piston provided with a sensing tip which is operated by the gas driving the piston. A force balance is maintained between the organ to which the device is applied, e.g., an eye, and the sensing tip of the device itself. That is, the force with which a membrane on the sensing tip is pushed against the eye is equal to the force with which a gas within the device pushes against the piston that drives the sensing tip.

In the pneumatic sensor described in U.S. Pat. No. 3,714,819 to Webb the approach used to ensure a stable reading was to provide a cylindrical arrangement for the probe wherein the latter was mounted for movement within the former by a pneumatic pressure, a leakage path being supplied for the operating gas from the cylinder through the piston to the tip. The piston was mounted within a cylinder for movement within a porous gas-permeable bearing, a porous bronze sleeve, which provided a film of gas upon which the piston rode with negligible friction. The free piston was prevented from separating from the mount by incorporation of a flange within the pressure chamber. The gas flow through the porous bronze sleeve passes partially to the pressure chamber and partially by venting along the piston to the outside atmosphere. The division of this flow between the two pathways is approximately equal when open to the atmosphere, but becomes unequal when pressure measurements are made. This inequality results from the back pressure developed in the pressure chamber. A probe of this general type is also described in Walker and Langham, Experimental Eye Research (1975) 20:167-172.

In the measurement of the fluid pressure in the eye using the above modified probes with a freely movable cylinder, potential errors became evident. First, the movement of the piston against the eye caused an increase of the pressure within the eye, i.e., a change in the pressure that was to be measured. This increase of the intraocular pressure resulted from the pressure developed within the chamber acting on the flange of the movable piston. This flange acted as a stop to prevent the piston moving out completely from the probe. The pressure exerted on the flange was transmitted to the footplate of the movable piston making contact with the cornea. The force acting on this footplate increased with the pressure developed within the pressure chamber, which in turn was a function of the pressure in the eye and also a function of the mechanical gain of the probe (the mechanical gain expresses the ratio of the intraocular pressure to that of the pressure chamber). In prior probes this ratio has been of the order of 0.5.

Examples of the disturbance of the intraocular pressure induced by the movement of the piston against the eyes of man and animals are summarized in FIGS. 1, 2, 3 and 4. FIGS. 1(a) to 1(d) show the pressure recorded internally in a human eye during the application of a pressure sensor. FIGS. 1(a) and 1(c) show that the prior art gas bearing pneumatic probe increased the intraocular pressure by 6 mmHg, i.e., from a set IOP of 15 mmHg to 21 mmHg during the period the probe was applied to the eye. In contradistinction, FIGS. 1(b) and 1(d) show that the present probe increased the set IOP of 15 mmHg by less than 1 mmHg.

The disturbance of the IOP by the application of the prior art probe to rabbit and cat eyes was more severe as indicated in FIGS. 2(a) and 2(b), respectively. For example, FIG. 2(a) shows that in rabbits with an average IOP of 20 mmHg the prior art probe caused the pressure to increase to more than 30 mmHg.

A second source of error in measurement of the intraocular pressure, using the gas bearing pneumatic probe, resulted in a marked curvilinearity of the calibration curve (FIGS. 3 and 4). This was due to the increased loss of gas flow through the pressure chamber at increased intraocular pressures. The increased intraocular pressure caused a throttling effect on the gas flow and as a consequence the venting of gas directly to the atmosphere increased proportionately. The magnitude of this loss, and as a consequence the size of the nonlinearity of the calibration curve is critically dependent on the geometry of the vent pathway. In practice this is difficult to control and as a consequence the curvilinearity of probes may differ significantly.

This source of error is eliminated in the present probe by elimination of the gas bearing piston system. FIGS. 3 and 5 show how the elimination of this gas leakage results in a linear calibration for the human eye using the present probe.

Accordingly, it is desirable to provide a pneumatic pressure probe which avoids the inherent errors of the prior art devices and provides a means for rapid and accurate measurement of fluid pressure through a body membrane. The present invention satisfies these desires.

SUMMARY OF THE INVENTION

The present invention is a pneumatic pressure probe that provides a relatively rapid and accurate measurement of fluid pressure within an organ, such as an eye or a blood vessel, without distorting the organ itself. The probe utilizes a sensor head that contacts the organ without applying thereto an error introducing force.

The pneumatic pressure probe of the present invention includes a hollow handle defining a pressure chamber and a forshortenable hollow shaft slidably received within the handle. The proximal end of the hollow shaft is in communication with the pressure chamber but is not influenced by the pressure developed within that chamber. A sensor head is mounted on the distal end of the hollow shaft and defines a contact face as well as a cavity that provides a venting chamber which extends to and terminates in a sensing aperture in the contact face. Optionally, the sensing aperture can be covered by a membrane. The hollow shaft extends into the cavity and terminates in a thrust nozzle that is substantially coplanar with a plane defined by the contact face.

In use, the contact face is placed in contact with the membrane surrounding an organ such as the eye but without distorting it. The thrust of the gas discharging from the thrust nozzle applies a limited force to the area of the epithelium of the membrane adjacent to the thrust nozzle without distorting the shape of the endothelium. As a result, no force is applied to the body fluid the pressure of which is to be measured. This is illustrated in FIGS. 1(b) and 1(d), in which the intraocular pressure of human eyes were recorded during the application of the probe to eyes with an intraocular pressure of 15 mmHg. It will be observed that the probe caused the intraocular pressures to increase by less than 1 mmHg.

The shaft allows the sensor head to move relative to the handle, however, thereby neutralizing the effect of hand movements of the operator.

The patient can be in a standing, sitting or supine position during the fluid pressure measurement.

Numerous other advantages and features of the present invention will become readily apparent from the following detailed description of the invention, the accompanying examples, the drawings and the appended claims.

BRIEF DESCRIPTION OF THE DRAWINGS

FIGS. 1(a) to 1(d) are graphical representations of performance data using a prior art pneumatic pressure probe and a pressure probe of the present invention. FIGS. 1(a) and 1(c) are graphical representations of performance data of a prior art gas bearing pneumatic probe showing a significant increase in the IOP when the prior art probe contacts the eye. FIGS. 1(b) and 1(d) are graphical representations of performance data of the present probe showing a minimal increase in the IOP when the present probe contacts the eye.

FIGS. 2(a) and 2(b) are graphical representations of performance data using a prior art pneumatic pressure probe to measure IOP in rabbit and cat eyes, respectively. The open points represent the intraocular pressure as determined by the prior art pressure probe. The filled in points represent the values of the intraocular pressure in the absence of a pressure disturbance. The pressure difference between the closed and the open points indicates the pressure increase induced in the eye by the prior art probe making contact with the eye. Data taken from Hammond and Bhattacherjee, Experimental Eye Research (1984) 39:791–805.

FIG. 7 is a perspective view of a pneumatic pressure probe embodying the present invention;

FIG. 8 is a fragmentary sectional view taken along plane 8—8 of FIG. 7 showing the internal detail of the sensor head and part of the handle of the pneumatic pressure probe embodying the present invention;

FIG. 9 is an enlarged perspective view of the sensor head embodying the present invention;

FIG. 10 is a sectional view of a sensor head of an alternative design embodying the present invention;

FIG. 11 is a fragmentary sectional view of a handle of an alternative design embodying the present invention;

FIG. 12 is a fragmentary sectional view showing a telescoping hollow shaft mounted in the handle of a pneumatic pressure probe embodying the present invention;

FIG. 13 is a fragmentary sectional view showing a reversibly axially collapsible hollow shaft mounted in the handle of a pneumatic pressure probe embodying the present invention;

FIG. 14 is an enlarged fragmentary view, in section, of the sensor head of FIG. 8 shown as applied to the cornea of an eye;

FIG. 15 is an enlarged fragmentary view, in section, of the sensor head of FIG. 10 shown as applied to the cornea of an eye;

DESCRIPTION OF THE PREFERRED EMBODIMENTS

Figure 4:
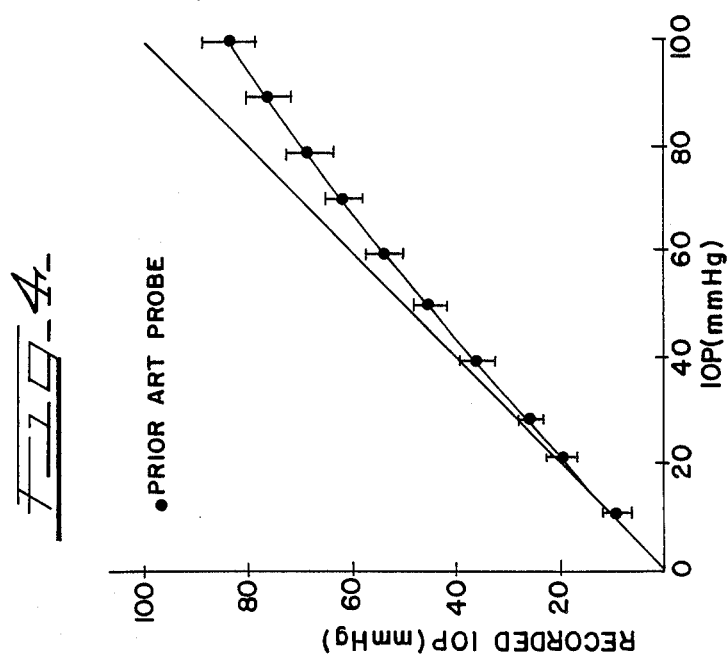
FIG. 4 is a graphical representation of performance data using a prior art pneumatic pressure probe indicating the relationship between set intraocular pressure and the recorded intraocular pressure utilizing a prior art gas bearing probe used on ten enucleated human eyes. Results taken from Langham and Tomey, Experimental Eye Research (1978) 27:17–25.
Figure 3:
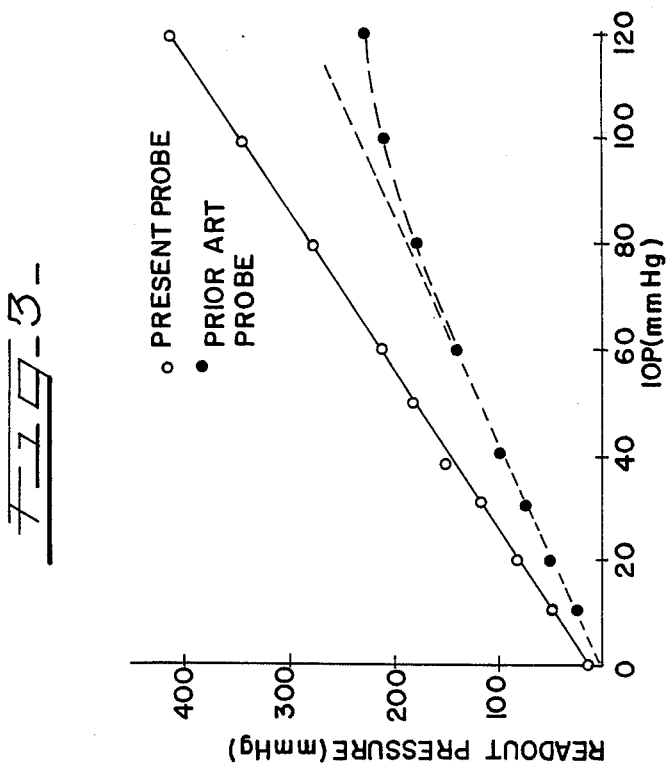
FIG. 3 is a graphical representation of performance data using a prior art pneumatic pressure probe and a pressure probe of the present invention showing a comparison of calibration data on the same human eye using a prior art gas bearing probe and the present probe.

While this invention is susceptible to embodiment in many different forms, there are shown in the drawings and will be described in detail, preferred embodiments of the invention. It should be understood, however, that the present disclosure is to be considered as an exemplification of the principles of this invention and is not intended to limit the invention to the embodiments illustrated.

One embodiment of the present invention, a pneumatic pressure probe 12, is shown in FIGS. 7-9. The pneumatic pressure probe 12 includes a hollow elongated handle 14, a hollow, elongated and foreshortenable shaft 24 having a proximal end 26 (FIG. 8) extending into the handle 14 and a sensor head 34 attached to the distal end 32 of the shaft 24.

The handle 14 defines therewithin a pressure chamber 16. A pressurizing gas passageway 18 is in communication with the pressure chamber 16 and adapted for operable association with a conventional pressurized gas source (not shown) for pressurizing the pressure chamber 16. A throttle means 22 in the pressurizing gas passageway 18 throttles the flow of gas to create a pressure gradient between the gas source and the pressure chamber 16. This pressure gradient insures a constant flow of gas which is minimally influenced by the pressure developed in the pressure chamber 16 as the instrument is used. Alternatively, the throttle means 22 may be located elsewhere between the gas source and the pressure chamber or it may be eliminated. A gas exit passageway 20 is in communication with the pressure chamber 16 and is adapted for communication with a conventional pressure transducer (not shown) for measuring the pressure within chamber 16.

The hollow handle 14 also defines a dampening chamber 28. Shaft 24 extends through this dampening chamber. Also, shaft 24 is forshortenable with respect to the handle 14 by being slidably received within the handle, thus allowing the contact face 36 to be kept in relatively stable contact with the body membrane notwithstanding gross movements of the hand of the operator. The mechanism by which the shaft 24 is foreshortened is not critical as long as it does not affect the pressure of the fluid to be measured. Proximal end 26 of the shaft 24 is in communication with the pressure chamber 16. There is substantially no gas leakage between the pressure chamber 16 and dampening chamber 28. A movement limiting means 30 affixed to the shaft 24 limits the movement of the sensor head 34 relative to the handle 14. A preferred movement limiting means 30 is a disk having a relatively low coefficient of friction (e.g., a disk made from a solid halogenated hydrocarbon polymer such as that commercially available under the designation "Teflon"). Because the disk is located in the dampening chamber 28, no force is applied thereto by the flowing gas, and thus the disk merely limits the movement of the sensor head 34 but does not transmit any force to the sensor head.

The sensor head 34 defines a substantially planar contact face 36 and a cavity that provides a venting chamber 44 which extends to and terminates in a sensing aperture 38 in contact face 36. Peripheral vents 42 are provided in sensor head 34 and are in communication with the venting chamber 44. The thrust nozzle 40 is a continuation of hollow shaft 24 and extends through the venting chamber 44. The thrust nozzle 40 is preferably coplanar with the contact surface 36 but may be slightly recessed from the plane defined by the contact face 36. This recess can be up to about 0.005 inches (0.013 cm).

While the contact face 36 can be applied directly to the walls of the membrane, this may be undesirable in some cases. In such instances a protective membrane 70, such as a smooth silastic, usually about 5 to 10 microns thick, fits over the contact face 36 without tension. The protective membrane 70 is held in position by a membrane retaining means shown here as a retaining clip 48 which reversibly cooperates with the peripheral groove 46. This clip may form part of the membrane. The venting chamber 44 is in communication with the pressure chamber 16 through the hollow shaft 24 and its terminal thrust nozzle 40.

FIG. 10 shows an alternative embodiment of a sensor head 134 that does not utilize a protective membrane. The thrust nozzle 140 is substantially coplanar with a plane defined by the contact face 136.

An alternative embodiment of a handle 214 is shown in FIG. 11. In this particular embodiment, the handle 214 only defines a pressure chamber 216 but not a dampening chamber. In communication with the pressure chamber 216 is the proximal end 226 of the foreshortenable shaft 224, slidably received within bore 225 of handle 214.

FIGS. 12 and 13 show alternative embodiments of the hollow, elongated and forshortenable shaft 24 as shown in FIGS. 7-9. In FIG. 12, shaft 324 is comprised of interactive elements 352, 354 and 356 which cooperate so as to allow shaft 324 to reversibly telescope. In FIG. 13, the shaft 424 has a reversibly collapsible section 460 which allows foreshortening.

The operation of the device of this invention will be shown with particular reference to FIG. 14 which, by way of example only, schematically shows the present sensor head while measuring intraocular pressure (IOP) within an eye. The total gas flow from the aforedescribed pressure chamber is directed through the hollow shaft 24 to the sensor head 34 where the gas discharges from the thrust nozzle 40. The contact face 36, covered by membrane 70, is placed against the epithelium 64 of the cornea 62 of an eye. The thrust from thrust nozzle 40 applies a force to the area of the epithelium 64 adjacent the thrust nozzle 40. As pressure builds within the venting chamber 44, the radius of curvature of the region of the epithelium 64 circumscribed by the sensing aperture 38 is somewhat reduced, but the radius of curvature of the endothelium 66 remains substantially unchanged. The epithelium 64 exerts a reaction force on the gas discharging from the thrust nozzle 40. This force, in turn, generates a pressure in the pressure chamber such as chamber 16 in FIG. 8. The pressure transducer attached to the gas exit passageway measures the pressure within the pressure chamber. The gas exits the sensor head 34 via vents 42. While the curvature of the area being used to determine the pressure in the eye is reduced, since the endothelium 66 is not flattened, the configuration and the pressure within the anterior chamber 72 (the chamber behind the cornea) of the eye are not influenced by the applied pressure probe.

The pressure measured by the transducer in the pressure chamber corresponds substantially to the instantaneous pressure within the eye. Accordingly, pressure fluctuations within the eye can be readily monitored and recorded. In this manner the eye of the patient can be utilized as a "built-in" transducer suitable for monitoring not only IOP, but the patient's circulatory system as well. To make a measurement of the IOP, the rate of mass flow through the thrust nozzle 40 is adjusted to provide a thrust or force against the cornea 62 of the eye sufficient to reduce the radius of curvature of the epithelium 64 of the cornea 62 without flattening the endothelium 66. During the course of a measurement, pressure within the venting chamber 44, and thus the pressure chamber in communication therewith, is maintained at a substantially constant level above atmospheric pressure In this manner the instantaneous fluctuation in pressure detected by the probe can be readily measured and recorded. The present configuration of the thrust nozzle 40 and the venting chamber 44 also permits an amplification of the detected instantaneous fluctuations. In particular, it has been found that the gain is a function of the area of the thrust nozzle 40 making contact with the cornea. Preferably a gain of about 2 to about 3 is utilized for IOP measurement. As used herein, the "gain" refers to the mechanical gain expressed as a ratio of the IOP to that of the pressure within the measuring device.

When the sensor head 134 is used as shown in FIG. 15, that is, without a protective membrane, the associated gas passageway, the pressure chamber, the hollow shaft 124, the vents 142 the gas exit passageway and the pressure transducer operate as previously described. The thrust of the gas discharging from the thrust nozzle 140 somewhat reduces the curvature of the epithelium 64 adjacent to the thrust nozzle 140 but does not affect the curvature of the endothelium 66. Only the area of the epithelium adjacent to the thrust nozzle 140 is affected.

The present pressure probe is particularly useful for determining the IOP and the oscillation of the IOP, i.e., the ocular pressure amplitude (PA), for diagnostic purposes.

The condition of the ocular perfusion pressure (the pressure of fluid flowing through the eye) is also assessable from the IOP and PA. For this purpose, the patient may be situated in any comfortable position during the pressure measurement. In this procedure, the PA of the patient's eyes are recorded at normal IOP's. The IOP is then raised to equal one half the brachial systolic arterial pressure. Convenient ways to raise the IOP include applying suction from a vacuum system to the eye or applying digital pressure to the upper and lower eyelids. The PA's are recorded at the raised IOP. In eyes with an ocular perfusion pressure that is equal to or exceeds the norm, the PA values are symmetrical in pairs of eyes under identical conditions and the PA's at the raised IOP are approximately 50% of the initial value.

On the other hand, in a patient suffering from narrowing of the internal carotid artery, the ophthalmic arterial pressure and ocular perfusion pressure is reflected as a decrease in the PA. If only one eye is affected, the PA readings will not be symmetrical in pairs of eyes under identical conditions. At the increased IOP, the PA of the affected eye is greatly less than its initial value and may go to zero. A PA of zero indicates that the ophthalmic arterial pressure is less than the IOP. This procedure allows rapid assessment of the ocular perfusion pressure which is an indication of the condition of the carotid and ophthalmic arteries.

Figure 5:
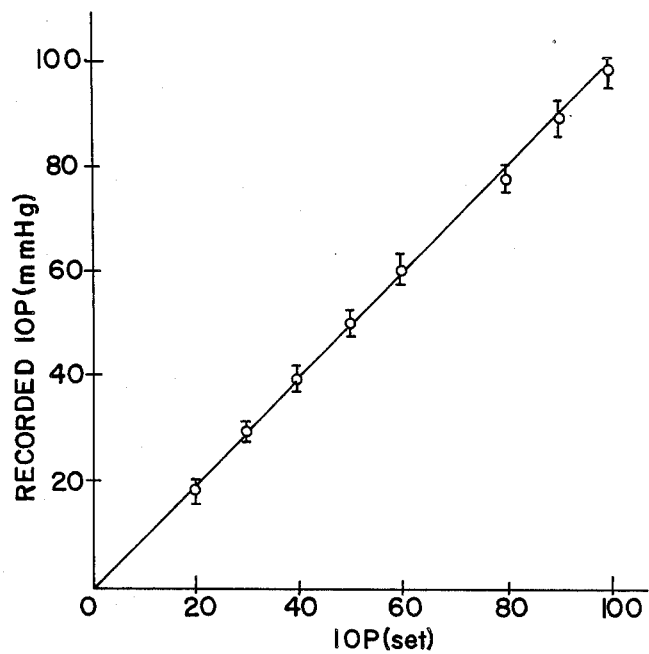
FIG. 5 is a graphical representation of the relationship between the set intraocular pressure and the recorded pressure using the present probe on ten enucleated human eyes.
Figure 6A:
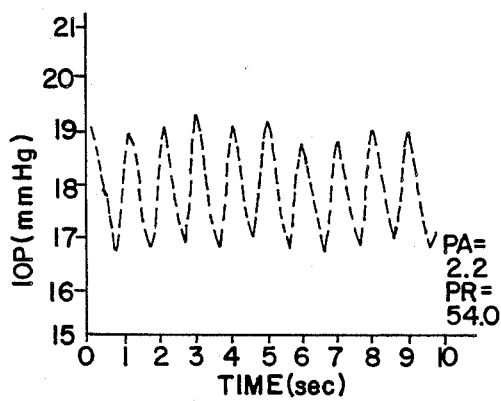
FIGS. 6(a) and 6(b) are graphical representations of recordings of the intraocular pressure in a seated, conscious human subject utilizing a probe embodying the present invention. Shown are the intraocular pressure pulse in an undisturbed eye [FIG. 6(a)] and in the same eye at an intraocular pressure equal to one half of the brachial arterial pressure [FIG. 6(b)].
Figure 6B:
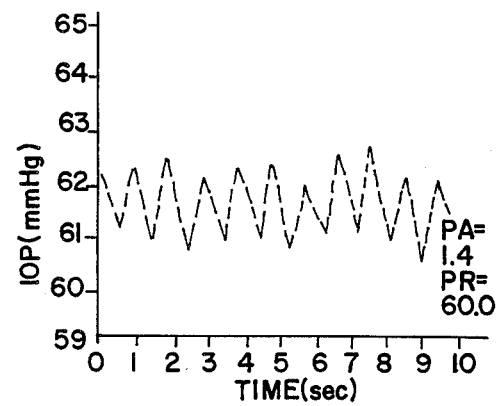

The accuracy of the present pneumatic pressure probe is dependent on maintaining an almost constant flow of gas through the sensor head. When this is achieved, there is a linear relationship between the intraocular pressure and the pressure in the pressure chamber as shown in FIG. 5. This linearity has not been found to exist in an air bearing pressure probe as can be seen from FIG. 4. In the latter, a deviation from linearity occurs with increasing levels of pressure within the eye.

The foregoing specification is intended as illustrative and is not to be taken as limiting. Still other variations within the spirit and scope of this invention are possible and will readily present themselves to those skilled in the art.

I claim:

1. A pneumatic pressure probe which comprises:
   a hollow elongated handle defining therewithin a pressure chamber, a pressurizing gas passageway in communication with the pressure chamber and adapted for operable association with a pressurized gas source for pressurizing the pressure chamber, and a gas exit passageway in communication with the pressure chamber and adapted for communication with a pressure transducer means;
   a hollow, elongated and foreshortenable shaft received in said handle, mounted so as to transmit no force from the pressure chamber, and having a proximal end extending into said pressure chamber while a distal end thereof extends beyond the handle; and
   a sensor head mounted to the distal end of said hollow shaft and defining a substantially planar contact face for placement on the epithelium of an organ, a cavity that provides a venting chamber which extends to and terminates in a sensing aperture in the contact face, and peripheral vent means in communication with the cavity;
   said shaft distal end extending into said cavity for a fixed distance and terminating in a thrust nozzle that is substantially coplanar with but does not extend beyond a plane defined by said contact face; and
   said pressure chamber being closed to the atmosphere and communicating with said cavity through said hollow shaft so that the total gas flow from the pressure chamber is through the hollow shaft to the sensor head.

2. The pneumatic pressure probe of claim 1 wherein said thrust nozzle is recessed from the plane defined by the contact face a distance of up to about 0.005 inches (0.13cm).

3. The pneumatic pressure probe of claim 1 wherein said sensor head further comprises a protective membrane retaining means for retaining a removable protective membrane in position over said contact face.

4. The pneumatic pressure probe of claim 3 wherein said protective membrane retaining means is defined by the sensor head as a peripheral groove and said protective membrane retaining means further comprises a retaining clip which removably cooperates with said groove.

5. The pneumatic pressure probe of claim 1 wherein said hollow shaft is slidably received in said handle.

6. The pneumatic pressure probe of claim 5 further comprising a movement limiting means for limiting the movement of said sensor head relative to said handle without transmitting any force to said sensor head.

7. The pneumatic pressure probe of claim 1 wherein said handle further defines therewithin a dampening chamber, wherein said proximal end of said hollow shaft extends through said dampening chamber and into said pressure chamber and there is substantially no gas leakage between the pressure chamber and the dampening chamber.

8. The pneumatic pressure probe of claim 7 wherein said hollow shaft is slidably received in said handle.

9. The pneumatic pressure probe of claim 8 further comprising a movement limiting means associated with said shaft for limiting the movement of said sensor head relative to said handle.

10. The pneumatic pressure probe of claim 9 wherein said movement limiting means is located within said dampening chamber.

11. The pneumatic pressure probe of claim 10 wherein said movement limiting means is a disc affixed to said hollow shaft.

12. The pneumatic pressure probe of claim 1 wherein said hollow shaft is a telescoping hollow shaft.

13. The pneumatic pressure probe of claim 1 wherein said hollow shaft is a reversibly collapsible hollow shaft.

14. The pneumatic pressure probe of claim 1 wherein said pressurizing gas passageway includes a throttle means for creating a pressure gradient between said gas source and said pressure chamber.

15. The pneumatic pressure probe of claim 1 wherein said shaft distal end extends through said venting chamber and said thrust nozzle is a continuation of said shaft.

* * * * *